(12) United States Patent
Astier et al.

(10) Patent No.: US 9,588,289 B1
(45) Date of Patent: Mar. 7, 2017

(54) COINTEGRATION OF OPTICAL WAVEGUIDES, MICROFLUIDICS, AND ELECTRONICS ON SAPPHIRE SUBSTRATES

(71) Applicant: International Business Machines Corporation, Armonk, NY (US)

(72) Inventors: Yann A. N. Astier, Irvington, NY (US); Ning Li, White Plains, NY (US); Devendra K. Sadana, Pleasantville, NY (US); Joshua T. Smith, Croton on Hudson, NY (US); William T. Spratt, Westchester, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/002,041

(22) Filed: Jan. 20, 2016

(51) Int. Cl.
  *G02B 6/13* (2006.01)
  *G02B 6/12* (2006.01)
  *G02B 6/136* (2006.01)
  *G02B 6/132* (2006.01)

(52) U.S. Cl.
  CPC ......... *G02B 6/12004* (2013.01); *G02B 6/131* (2013.01); *G02B 6/132* (2013.01); *G02B 6/136* (2013.01); *G02B 2006/121* (2013.01); *G02B 2006/12035* (2013.01); *G02B 2006/12038* (2013.01); *G02B 2006/12061* (2013.01); *G02B 2006/12104* (2013.01); *G02B 2006/12197* (2013.01)

(58) Field of Classification Search
  CPC ...................................................... B82Y 20/00
  See application file for complete search history.

(56) References Cited

U.S. PATENT DOCUMENTS

| 5,238,877 | A | 8/1993 | Russell |
| 6,100,541 | A | 8/2000 | Nagle et al. |
| 7,087,444 | B2 * | 8/2006 | Wong ................ B01L 3/502707 438/16 |
| 7,309,620 | B2 * | 12/2007 | Fonash ................. B81C 99/008 257/E21.151 |
| 7,319,046 | B2 | 1/2008 | Misiakos et al. |
| 8,137,981 | B2 | 3/2012 | Andrew et al. |
| 8,282,882 | B2 * | 10/2012 | Chakravarty .......... B82Y 20/00 385/12 |
| 2007/0140638 | A1 | 6/2007 | Yang et al. |

(Continued)

FOREIGN PATENT DOCUMENTS

CN 103760336 A 4/2014
KR 100785027 B1 12/2007

*Primary Examiner* — Robert Carpenter
(74) *Attorney, Agent, or Firm* — Scully, Scott, Murphy & Presser, P.C.; Louis J. Percello, Esq.

(57) ABSTRACT

A method of forming a semiconductor structure includes forming a first optical waveguide and a second optical waveguide on a sapphire substrate. The first optical waveguide and the second optical waveguide each include a core portion of gallium nitride (GaN), and a cladding layer laterally surrounding the core portion. The cladding layer includes a material having a refractive index less than a refractive index of the sapphire substrate. The method further includes etching a portion of the cladding layer to form a microfluidic channel therein and forming a capping layer on a top surface of the first optical waveguide, the second optical waveguide and the microfluidic channel.

6 Claims, 11 Drawing Sheets

(56) References Cited

U.S. PATENT DOCUMENTS

2008/0204709 A1 8/2008 Kiesel et al.
2009/0263912 A1 10/2009 Yang et al.
2013/0011914 A1 1/2013 Kim

* cited by examiner

US 9,588,289 B1

COINTEGRATION OF OPTICAL WAVEGUIDES, MICROFLUIDICS, AND ELECTRONICS ON SAPPHIRE SUBSTRATES

BACKGROUND

The present application relates to the integration of optical waveguides and micro-or-nano fluidics on a single wafer, and more particularly to optical waveguides including gallium nitride (GaN) core portions combined with microfluidics (e.g., in silicon (Si) or silicon dioxide ($SiO_2$)) and electronics integrated together on a same wafer.

The integration of optical waveguides and micro-or-nano fluidics on a single wafer is highly desirable for medical, biological, and chemical applications. Micro-fluidics are commonly made in silicon. However, silicon, which does not lend itself to infrared (IR) waveguides, is absorptive in the ultraviolet (UV) range and many biological optical methods are based in the UV spectrum. Thus, due to silicon's absorption in the visual/UV range, silicon may not be used for visual/UV waveguides.

Also, conventional detection and fluidic systems vary from lab size (e.g., microscopes and bench top instruments) to small systems (e.g., fiber based, briefcase size or small suitcase sized). There is still a need in the art however for smaller sized detection and fluidic systems which, for example, can enable a smart phone.

SUMMARY

In accordance with an aspect of the present application, methods of forming a semiconductor structure are provided. In one embodiment of the present application, the method may include forming a first optical waveguide and a second optical waveguide on a sapphire substrate. The first optical waveguide and the second optical waveguide each include a core portion of gallium nitride (GaN), and a cladding layer laterally surrounding the core portion. The cladding layer includes a material having a refractive index less than a refractive index of the sapphire substrate. Next, a portion of the cladding layer is etched to form a microfluidic channel therein, and thereafter a capping layer is formed on a top surface of the first optical waveguide, the second optical waveguide and the microfluidic channel.

In accordance with another embodiment, the method may include forming a first optical waveguide and a second optical waveguide on a sapphire substrate. The first optical waveguide and the second optical waveguide each include a core portion of gallium nitride (GaN), and a cladding layer laterally surrounding the core portion. The cladding layer includes a material having a refractive index less than a refractive index of the sapphire substrate. The method of this embodiment further includes epitaxially growing a bonding layer on a silicon substrate. The bonding layer is then etched to transform the bonding layer into a patterned bonding layer having a microfluidic channel therein. Next, one of the silicon substrate or the sapphire substrate is flipped and the patterned bonding layer and the microfluidic channel located on the silicon substrate are bonded to top surfaces of first optical waveguide and the second optical waveguide located on the sapphire substrate in a flip chip bonding process.

In accordance with another aspect of the present application, a semiconductor structure is provided. In one embodiment, the semiconductor structure may include a first optical waveguide and a second optical waveguide located on a sapphire substrate. The first optical waveguide and the second optical waveguide each include a core portion of gallium nitride (GaN), and a cladding layer laterally surrounding the core portion. The cladding layer includes a material having a refractive index less than a refractive index of the sapphire substrate.

The semiconductor structure may further include a microfluidic channel located on a portion of the sapphire substrate and operatively connected to the first optical waveguide and the second optical waveguide, and a cover structure covering the top surface of the microfluidic channel and top surfaces of the first optical waveguide and the second optical waveguide. The cover structure includes a material having a refractive index less than the refractive index of the sapphire substrate.

DETAILED DESCRIPTION

Figure 1A:
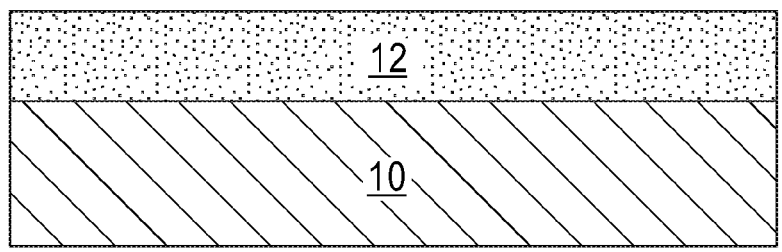
FIG. 1A is a cross-sectional view illustrating a GaN layer epitaxially grown on a sapphire substrate in accordance with a first embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Figure 1B:
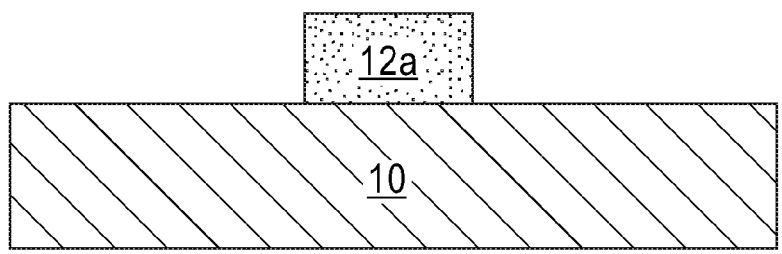
FIG. 1B is a cross-sectional view illustrating a first waveguide core portion of GaN formed on the sapphire substrate illustrated in FIG. 1A.
Figure 1C:
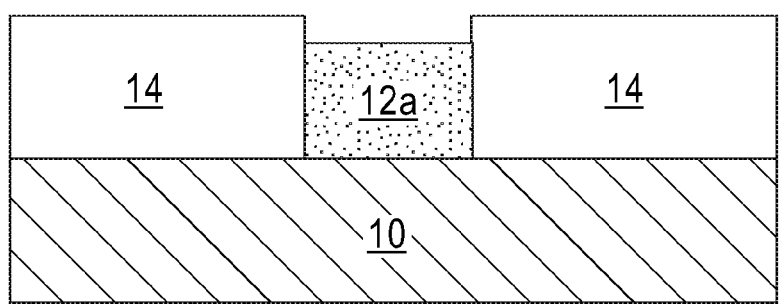
FIG. 1C is a cross-sectional view illustrating the depositing of a cladding material on the sapphire substrate of the structure illustrated in FIG. 1B.
Figure 1D:
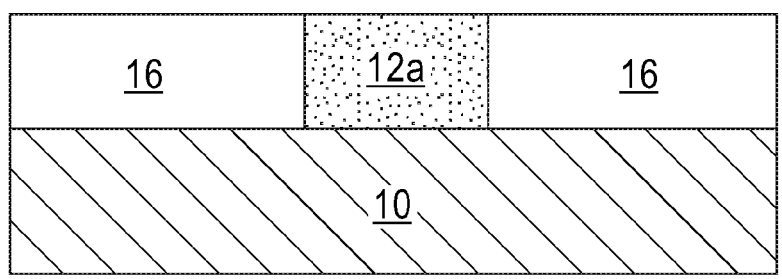
FIG. 1D is a cross-sectional view illustrating the planarization of the cladding material of the structure illustrated in FIG. 1C.
Figure 1E:
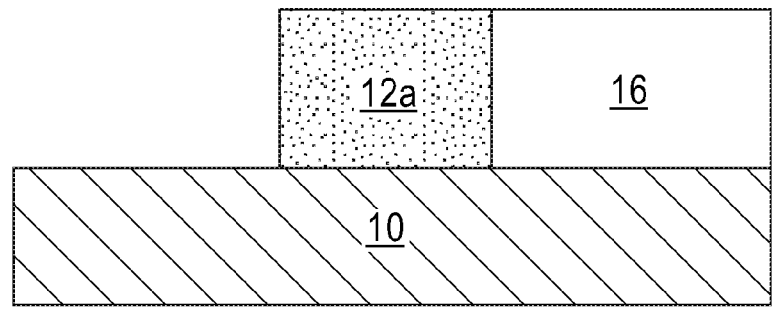
FIG. 1E is a cross-sectional view illustrating the etching of a portion of the cladding layer of the structure illustrated in FIG. 1D.
Figure 1F:
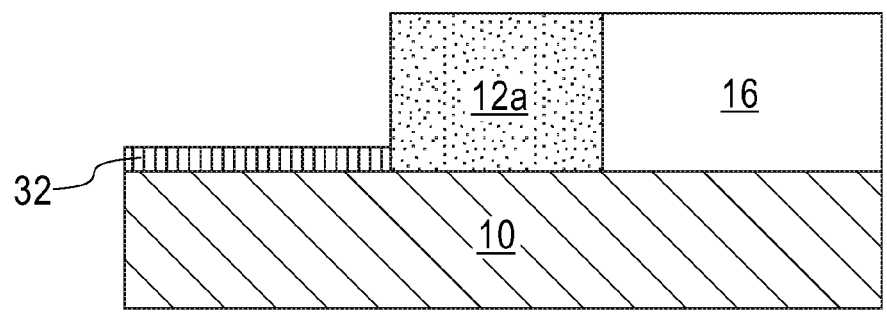
FIG. 1F is a cross-sectional view illustrating the depositing of a seed layer on the sapphire substrate of the structure illustrated in FIG. 1E.
Figure 1G:
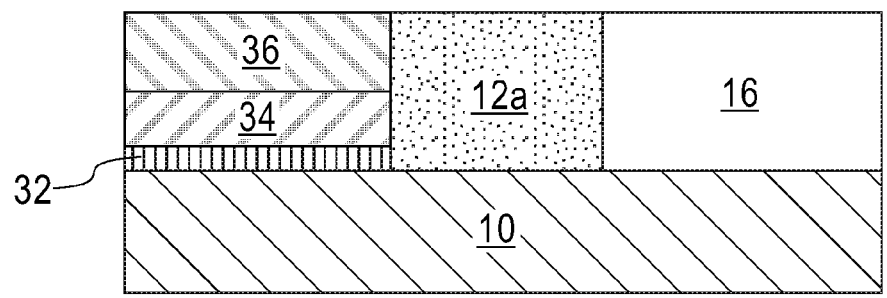
FIG. 1G is a cross-sectional view illustrating the forming of an lower GaN layer of a first conductivity type on the seed layer and an upper GaN layer of a second conductivity type, which is opposite the first conductivity type, on the lower GaN layer of the structure illustrated in FIG. 1F.
Figure 1H:
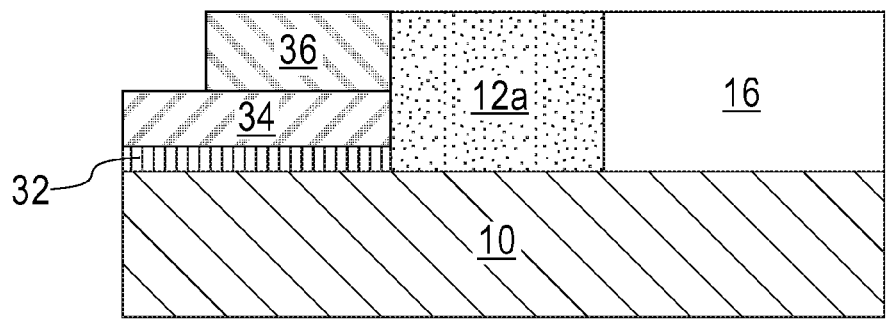
FIG. 1H is a cross-sectional view illustrating the etching of the upper GaN of the structure illustrated in FIG. 1G.
Figure 1I:
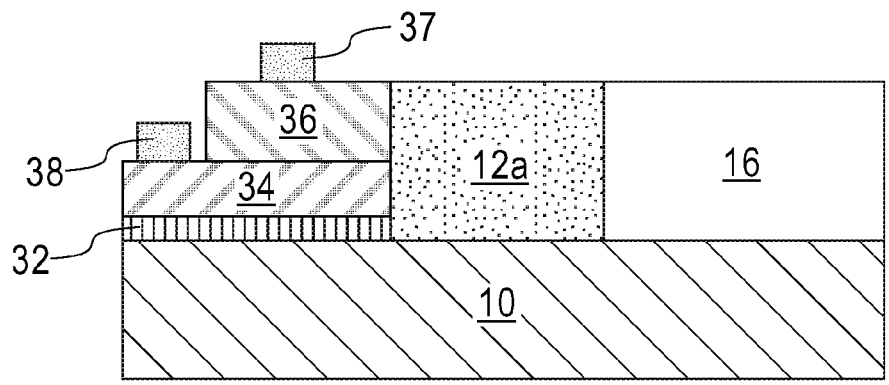
FIG. 1I is a cross-sectional view illustrating the forming of a first contact on the upper GaN layer and a second contact on the lower GaN layer of the structure illustrated in FIG. 1H.
Figure 1J:
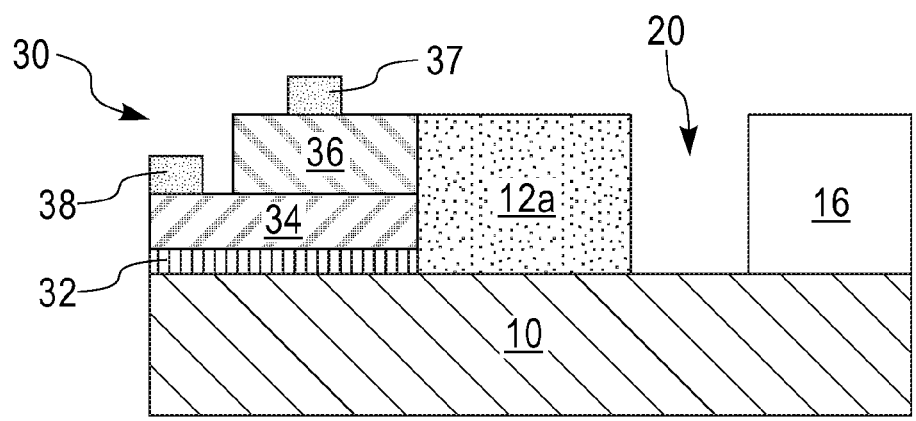
FIG. 1J is a cross-sectional view illustrating the etching of the cladding layer to form a microfluidic channel therein of the structure illustrated in FIG. 1I.
Figure 1K:
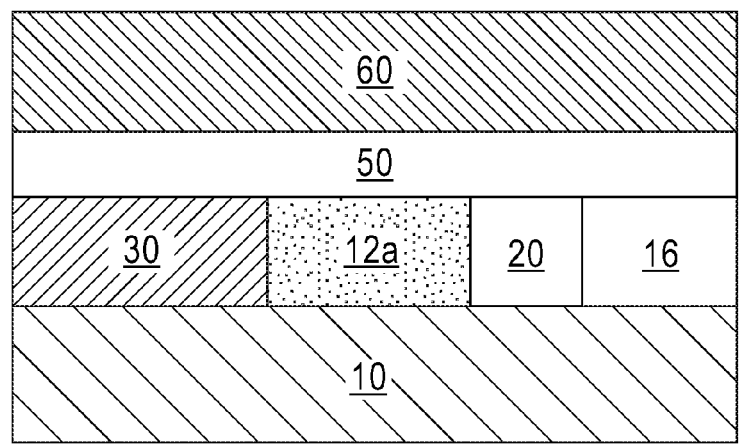
FIG. 1K is a cross-sectional view illustrating the bonding of a support substrate and a capping layer to the structure illustrated in FIG. 1J.
Figure 1L:
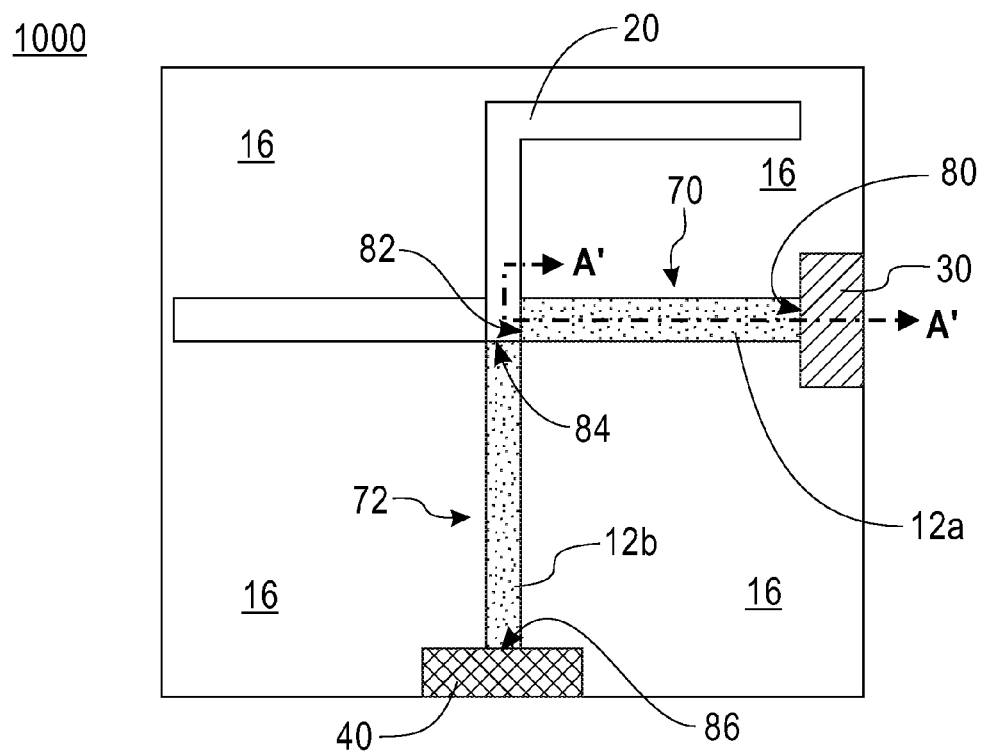
FIG. 1L is a top down view of the first semiconductor structure.
Figure 1M:
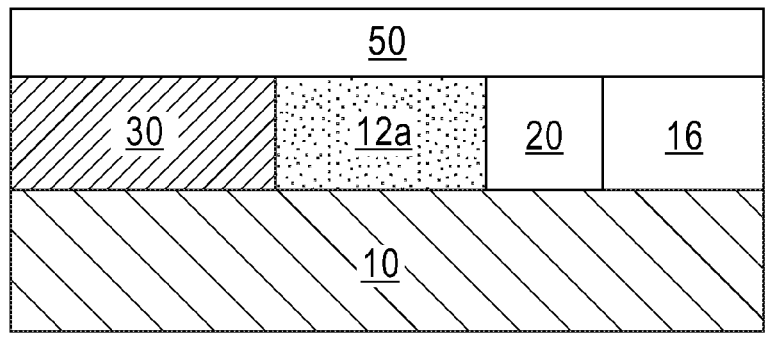
FIG. 1M is a cross-sectional view taken along line A'-A' of the first semiconductor structure illustrated in FIG. 1L.
Figure 1N:
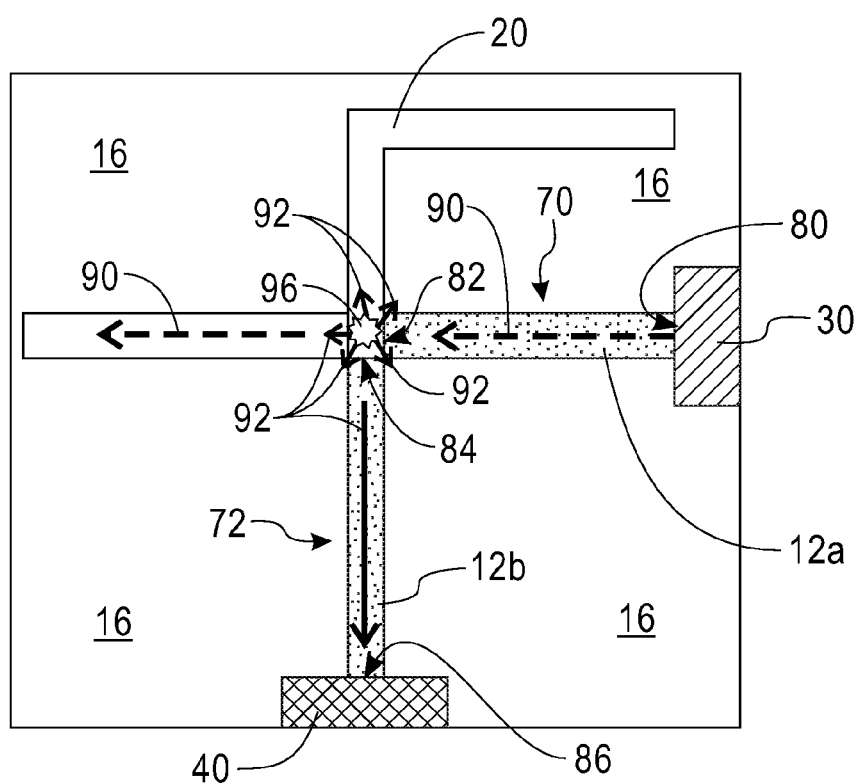
FIG. 1N is a top down view illustrating an example of the operation of the first semiconductor structure.

Referring now to FIGS. 1A-1N, there are shown a method of forming a first semiconductor structure 1000 (e.g., biosensor device) by co-integrating optical waveguides, microfluidic channels, and electronics on sapphire substrates according to a first embodiment of the present application.

Referring to FIG. 1A, an epitaxial growth process is performed to grow a gallium nitride (GaN) layer 12 on a substrate 10. For example, in performing the epitaxial growth process, a seed layer (not shown) may first be deposited on the substrate 10. A GaN material is then epitaxially grown on the seed layer to provide the GaN layer 12. In the present embodiment, the substrate 10 is a sapphire substrate (hereinafter referred to as the "sapphire substrate 10"). In addition, the seed layer may include, for example, aluminum nitride (AlN). The epitaxial growth process for forming the GaN layer 12 on the sapphire substrate 10 may include, for example, MOCVD (metal organic chemical vapor deposition) or MBE (molecular beam epitaxy).

Referring now to FIG. 1B, the GaN layer 12 is then etched using, for example, one of a reactive ion etching (RIE) or a wet etching process to define a first optical waveguide core portion 12a of GaN and a second optical waveguide core portion 12b of GaN (See FIGS. 1L and 1N) on the sapphire substrate 10. As shown in FIGS. 1L and 1N, the first waveguide core portion 12a and the second waveguide core portion 12b have an orthogonal orientation relative to one another to define an "L" type shape in the present embodiment. The orthogonal orientation of the first waveguide core portion 12a and the second waveguide core portion 12b may prevent direct illumination of the collection waveguide (e.g., second optical waveguide 12b) by a light source thereby increasing the sensitivity of the device. However, exemplary embodiments of the present application are not limited to the above mentioned configuration for the first optical waveguide core portion 12a and the second optical waveguide core portion 12b, but rather the first waveguide core portion 12a and the second waveguide core portion 12b may have different configurations in relation to one another as explained in further detail hereinafter in other embodiments.

Referring now to FIG. 1C, a backfill process is then performed by depositing a cladding material 14 onto the structure illustrated in FIG. 1B to fill in all areas on the top surface of the sapphire substrate 10 not occupied by the first waveguide core portion 12a and the second waveguide core portion 12b. A suitable cladding material 14 includes, for example, silicon dioxide ($SiO_2$), silicon nitride (SiN), glass or a polymer (e.g., polymethylmethacrylate (PMMA)). It is noted that the cladding material 14 is not limited to the above-mentioned materials, but rather can be any material having a lower refractive index than a refractive index of the sapphire substrate 10 and GaN to ensure wave guiding. In one embodiment, the cladding material 14 includes silicon dioxide ($SiO_2$).

According to an exemplary embodiment, the cladding material 14 is deposited using, for example, a plasma enhanced chemical vapor deposition (PECVD) sputtering process. As shown in FIG. 1C, the cladding material 14 is overgrown.

Referring now to FIG. 1D, the cladding material 14 is then planarized, using, for example, a chemical mechanical polishing process (CMP), to form a cladding layer 16 laterally surrounding the first waveguide core portion 12a and the second waveguide core portion 12b, thereby completing the formation of a first optical waveguide 70 and a second optical waveguide 72. (See also FIGS. 1L and 1N). Further, as shown in FIGS. 1D, 1L and 1N, the top surfaces of the cladding layer 16 are coplanar with the top surfaces of the first waveguide core portion 12a and the second waveguide core portion 12b. The first optical waveguide 70 includes the first optical waveguide core portion 12a and the portions of the cladding layer 16 surrounding the first optical waveguide core portion 12a. The second optical waveguide 72 includes the second optical waveguide core portion 12b and the portions of the cladding layer 16 surrounding the second optical waveguide core portion 12b.

Further, and if desired, electronics devices such as, for example, a light source (e.g., laser diode (ALD) or a light-emitting diode (LED) device) and/or a photodetector (e.g., a PIN photodiode or an avalanche photodiode (APD)) may then be fabricated on the sapphire substrate 10 including the first optical waveguide 70 and the second optical waveguide 72 during the fabrication of the first semiconductor structure 1000 such that the electronic devices and the first optical waveguide 70 and the second optical waveguide 72 are co-integrated on a same wafer.

Alternatively, and in other embodiments, electronic devices such as a light source and/or a photodetector may be formed in a separate process (e.g., packaged externally) from the formation of the first semiconductor structure 1000. In such cases in which the light source and/or photodetector are packaged externally from the formation of the first semiconductor structure 1000, the light source and/or photodetector could later be bonded to the first semiconductor structure using, for example, an epoxy resin, or the light source and/or photodetector may be placed at a location external to the first semiconductor structure 1000.

In the present embodiment, a light source 30 (e.g., LED) can be formed on the sapphire substrate 10 during the fabrication of the first semiconductor structure 1000. For example, a process for forming the light source 30 on a region of the sapphire substrate 10 is described in connection with FIGS. 1E-1I.

Referring to FIG. 1E, a hard mask layer (not shown) is disposed to cover substantially the entire top surfaces of the cladding layer 16 and the first optical waveguide core portion 12a and the second optical waveguide core portion 12b of the structure illustrated in FIG. 1D. A photoresist layer (not shown) is then formed on the hard mask layer. The photoresist layer is patterned to form a photoresist (not shown), and then the pattern from the photoresist is transferred into the hard mask layer to form a hard mask (not shown) which exposes a portion of the top surface of the cladding layer 16 of the structure illustrated in FIG. 1D in a region in which the light source 30, (i.e., LED) is to be formed using conventional photolithography and etching techniques.

The region chosen for the formation of the light source 30 in the present embodiment is next to an outlet 80 of the first waveguide core portion 12a in which excited light exiting from the light source 30 enters the first waveguide core portion 12. (See FIGS. 1L and 1N). A portion of the cladding layer 16 exposed by the hard mask is then etched away using the hard mask as an etching mask in, for example, an RIE or wet etching process to expose a portion of the top surface of the sapphire substrate 10, as shown in FIG. 1E.

Referring now to FIG. 1F, a seed layer 32 such as, for example, AlN, is then deposited on the exposed top surface of the sapphire substrate 10.

Referring now to FIG. 1G, a lower GaN layer 34 of a first conductivity type is then epitaixally grown on the seed layer 32 using, for example, MOCVD. In one embodiment, the lower GaN layer 34 is N-doped with Si dopants. The lower GaN layer 34 may be doped in-situ, or alternatively the lower GaN layer may be doped subsequently to its formation using an ion implantation process or a gas phase doping process. Further, an upper GaN layer 36 of a second conductivity type that is opposite the first conductivity type, is then epitaxially grown on the lower GaN layer 34 using, for example, MOCVD. In the illustrated embodiment, the upper GaN layer 36 is P-doped with magnesium (Mg) dopants. The upper GaN layer 36 may be doped in-situ, or alternatively the upper GaN layer 36 may be doped subsequently using an ion implantation process or gas phase doping. P-type dopant refers to the addition of an impurity to create deficiencies of valence electrons. N-type dopant refers to the addition of impurities which contribute more electrons to the semiconductor material. In some embodiments, the lower CaN layer 34 contains a P-type dopant, and the upper GaN layer 26 contains an N-type dopant.

Referring now to FIG. 1H, the photoresist and hard mask are then removed using conventional processes known in the art. Subsequently, another hard mask layer (not shown) and another photoresist layer (not shown) are sequentially deposited on the top surface of the upper GaN layer 36. The photoresist layer is patterned to form a photoresist (not shown), and then the pattern from the photoresist is transferred into the hard mask layer to form a hard mask (not shown) which exposes a portion of the top surface of the upper GaN layer 36. Then, using the hard mask as an etching mask, the exposed portion of the upper GaN layer 36 is etched using, for example, an RIE etching process to expose a portion of the top surface of the lower GaN layer 34. The hard mask and the photoresist are then removed from the upper GaN layer 36 using conventional methods known in the art.

Referring now to FIG. 1I, a first contact 37 can be formed on the top surface of the upper GaN layer 36, and a second contact 38 can be formed on the exposed portion of the top surface of the lower GaN layer 34. The first contact 37 and the second contact 38 may be formed by any chemical or physical vapor deposition method, such as electron-beam evaporation, filament evaporation, or sputter deposition. In addition, the first contact 37 and the second contact 38 may be formed of, for example, a metal or a metal alloy. In the present embodiment, the first contact 37 and the second contact 38 each include, for example, a palladium (Pd)/gold (Au) alloy. Conventional steps known in the art may then be performed to complete the light source 30. In one embodiment, the first contact 37 is the anode of the light source 30 and the second contact 38 is the cathode of the light source 30.

At this stage and after forming the light source 30, other electronic devices such as a photodetector may be formed on the structure illustrated in FIG. 1. As shown in FIGS. 1L and 1N, a photodetector 40 can be provided to the first semiconductor structure 1000. In an embodiment, the photodetector 40 may be formed of GaN and integrated with the first and second optical waveguides 70, 72 on the same wafer during the formation of the first semiconductor structure 1000 in a similar process as described above in connection with forming the light source 30 as would be understood by one of ordinary skill in the art. In other embodiments, the photodetector 40 may be formed of, for example, silicon and integrated with the first and second optical waveguides 70, 72 on the same wafer during the formation of the first semiconductor structure 1000 using a conventional process for forming photodetectors. In other embodiments, the photodetector 40 could instead be packaged externally from the processes for forming the first semiconductor structure 1000 and later be bonded to the first semiconductor structure using, for example, an epoxy resin. In still other embodiments, the photodetector 40 may be placed at a location external to the first semiconductor structure 1000. A discussion of how the photodetector 40 is formed has been omitted for the sake of brevity as it would be understand by one of ordinary skill in the art.

Referring now to FIG. 1J, and after forming the electronic devices (e.g., light source 30), a microfluidic channel 20 is formed in a region of the structure. In particular, a portion of the cladding layer 16 is patterned using, for example, a photoresist (not shown) and hard mask (not shown) and then an etch such as, for example, an RIE or wet etching process can be performed to form a microfluidic channel 20 in the cladding layer 16. The microfluidic channel 20 may be formed having a depth of, for example, 10 µm (micrometers) to 500 µm. The microfluidic channel 20 can contain analytes to be analyzed therein as will be discussed in more detail hereinafter. In other embodiments, the microfluidic channel 20 may instead be formed in a portion of the cladding layer 16 prior to forming electronic devices such as the light source 30 on the sapphire substrate 10.

Referring now to FIG. 1K, a capping layer 50 is formed on a support substrate 60 using an epitaxial growth process such as, for example, MOCVD. In one embodiment, the second substrate 60 includes, for example, Si, and the capping layer 50 includes, for example, $SiO_2$. Alternatively, and in other embodiments, the capping layer 50 may include, for example, glass, SiN or a polymer (e.g., PMMA). The structure including the capping layer 50 located on the support substrate 60 may be flipped and bonded to the structure illustrated in FIG. 1J using a conventional flip chip bonding process such that the capping layer 50 contacts the top surface of the cladding layer 16, the top surface of the first waveguide core portion 12a, the top surface of the second waveguide core portion 12b, and the top surface of the light source 30.

In some embodiments in which the electronic devices such as the light source and photodetector are not formed during the fabrication of the first semiconductor structure 1000, but rather are packaged externally from the first semiconductor structure 1000, the processes described in connection with FIGS. 1E-1I may be omitted and instead the method could proceed directly to the processes described in FIG. 1J for forming the microfluidic channel 20 in the cladding layer 16.

Referring back to the present embodiment, the support substrate 60 can be removed from the structure illustrated in FIG. 1K using conventional methods known in the art to form the first semiconductor structure 1000 illustrated in FIGS. 1L-1N. Moreover, if desired, the sapphire substrate 10 may be de-bonded and reused after the process for forming the first semiconductor structure 1000 is completed.

The first semiconductor structure 1000 includes a first optical waveguide 70, a second optical waveguide 72, a microfluidic channel 20, a light source 30 and a photodetector 40 each disposed on the top surface of the sapphire substrate 10. The first semiconductor structure 1000 further includes a capping layer 50 located on the top surfaces of the first waveguide 70, the second waveguide 72, the microfluidic channel 20, the light source 30 and the photodetector 40.

The first optical waveguide 70 includes the first optical waveguide core 12a, and the portions of the cladding layer 16 laterally surrounding the first optical waveguide core 12a. The second optical waveguide 72 includes the second optical waveguide core 12b, and the portions of the cladding layer 16 laterally surrounding the second optical waveguide core 12b. The first and second optical waveguides 70, 72 each have a size of, for example, 1 µm to 50 µm.

The microfluidic channel 20 of the first semiconductor structure 1000 is located in the cladding layer 16 and is operatively connected to the first optical waveguide 70 and the second optical waveguide 72. In particular, the first optical waveguide core 12a includes an inlet 80 connected to the light source 30 through which light (e.g., ultraviolet (UV) light, infrared (IR) light or visible light) emitted from the light source 30 enters into the first optical waveguide core 12a, and an outlet 82 through which the light (e.g., UV light, IR light, or visible light) guided by the first optical waveguide core 12a of the first optical waveguide 70 exits into the microfluidic channel 20.

Further, the second optical waveguide core 12b includes an inlet 84 connected to the microfluidic channel 20 such that excited light (e.g., light emitted from the light source 30 that is absorbed and excited by particles attached to an analyte flowing in the microfluidic channel 20) and non-excited light (e.g., light emitted from the light source 30 that is not absorbed by the particles attached to the analyte flowing the microfluidic channel 20 and that remains unchanged) exiting the microfluidic channel 20 can enter the second optical waveguide core 12b. In addition, the second optical waveguide core portion 12b further includes an outlet 86 connected to the photodetector 40 such that light guided through the second optical waveguide core 12b can exit the second optical waveguide core 12b through outlet 86 and into the photodetector 40. The photodetector 40 converts the excited light received from the second optical waveguide core 12b into an electrical signal for analysis as explained in further detail hereinafter.

As mentioned above, the first waveguide core portion 12a of the first optical waveguide 70 and the second waveguide core portion 12b of the second optical waveguide 72 have an orthogonal orientation relative to one another in the present embodiment. The orthogonal orientation of the first waveguide core portion 12a and the second waveguide core portion 12b may prevent direct illumination of the collection waveguide (e.g., second optical waveguide 12b) by the light source 30 thereby increasing the sensitivity of the device.

Now referring to FIG. 1N, the operation of the first semiconductor structure 1000 of the present embodiment will be described by way of a non-limiting example. In some embodiments, the first semiconductor structure 1000 is a biosensor chip which may be used to analyze biological analytes, but exemplary embodiments are not limited thereto. In the present embodiment, particles 96 (e.g., fluorescent particles) are attached to some analyte (not shown) of interest such as, for example, deoxyribonucleic acid (DNA), ribonucleic acid (RNA), proteins, viruses, etc., using conventional techniques known in the art.

In the present example, the particles 96 attached to the analytes emit fluorescent light in the UV range when excited by UV excitation light. Alternatively, and in other embodiments, the particles attached to the analyte may emit IR or visible light.

The analytes and particles 96 attached thereto flow in the microfluidic channel 20 of the first semiconductor structure 1000 using conventional techniques and materials. The light source 30 emits an excitation light 90 (e.g., UV light) which enters the first optical waveguide core portion 12a of the first optical waveguide 70 though inlet 80 and the excitation light 90 is guided by the first optical waveguide core portion 12a and through outlet 82 into microfluidic channel 20. In the microfluidic channel 20, some of the excitation light 90 gets absorbed by the particles 96 attached to the analytes to emit fluorescent UV light 92 having a different wavelength than the excitation light 90, and some of the excitation light 90 does not get absorbed by any of particles 96 attached to the analytes.

As shown in FIG. 1N, excitation light 90 absorbed by the particles 96 gets emitted by the particles 96 as fluorescent UV light 92 having a different wavelength than the excitation light 90 in several different directions such that (i) some of the emitted fluorescent UV light 92 is emitted into the second optical waveguide core portion 12b of the second optical waveguide 72, (ii) some of the emitted fluorescent light 92 travels into other areas of the microfluidic channel 20, and (iii) some of the emitted fluorescent light 92 travels into the cladding layer 16 of the first and second optical waveguides 70, 72.

The fluorescent UV light 92 emitted into the second optical waveguide core portion 12b is guided through the second optical waveguide core portion 12b and into the photodetector 40. Moreover, some of the excited light 90 not absorbed by the particles 96 of the analytes may also be scattered into the second optical waveguide core portion 12b of the second optical waveguide 72 due to other types of particles (e.g., inert particles that do not fluoresce) or air bubbles in the microfluidic channel 20. The effect of the excitation light 90 reaching the photodetector 40 may be minimized through the use of optical filters (not shown) which prevent the flow of the excitation light 90 not absorbed by particles 96 into the photodetector 40.

A method of fabricating the first semiconductor structure 1000 according a second embodiment of the present application is described in connection with FIGS. 2A-2D and FIGS. 1E-1N. The method of the present embodiment is substantially the same as the method of the first embodiment for fabricating the first semiconductor structure 1000 except that in the present embodiment the cladding material is deposited prior to the (GaN layer, as explained in further detail below. Otherwise all other steps in forming the first semiconductor structure 1000 of the present embodiment are the same as well as the method steps of the first embodiment.

Figure 2A:
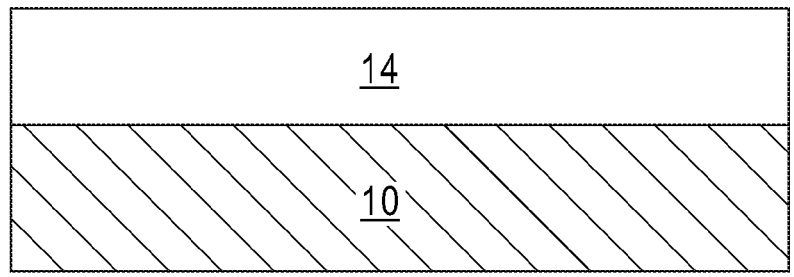
FIG. 2A is a cross-sectional view illustrating the depositing of a cladding material on a sapphire substrate according to a second embodiment of the present application.

Referring first to FIG. 2A, a cladding material 14 such as, for example, SiO$_2$ is deposited on a sapphire substrate 10 using, for example, a CVD process. Unlike the method of the first embodiment, the cladding material 14 of the present embodiment is formed prior to depositing GaN used to form the first waveguide core portion 12a and the second waveguide core portion 12b.

Figure 2B:
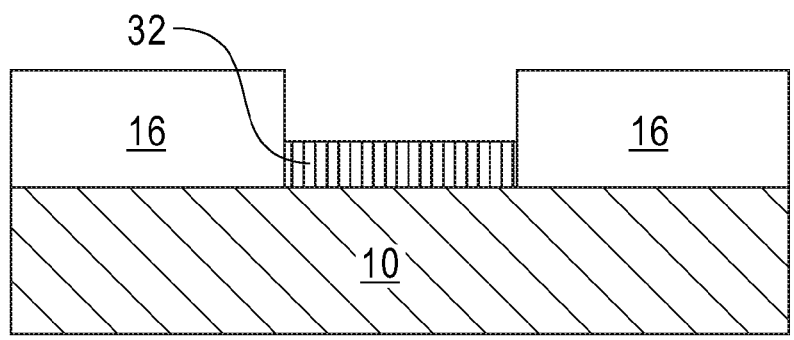
FIG. 2B is a cross-sectional view illustrating the etching of a portion of the cladding material and depositing a seed layer on the sapphire substrate of the structure illustrated in FIG. 2A.

Referring now to FIG. 2B, the cladding material 14 is then etched using, for example, e-beam/optical lithography and etching (e.g., RIE etching) in a region in which the first optical waveguide 70 and the second optical waveguide 72 are to be located on the sapphire substrate 10. The cladding material 14 is transformed into a cladding layer 16 by the RIE etching process. Further, a seed layer 32 formed of, for example, aluminum nitride (AlN) is then disposed on the sapphire substrate 10 in gaps that are located between the portions of the cladding layer 16.

Figure 2C:
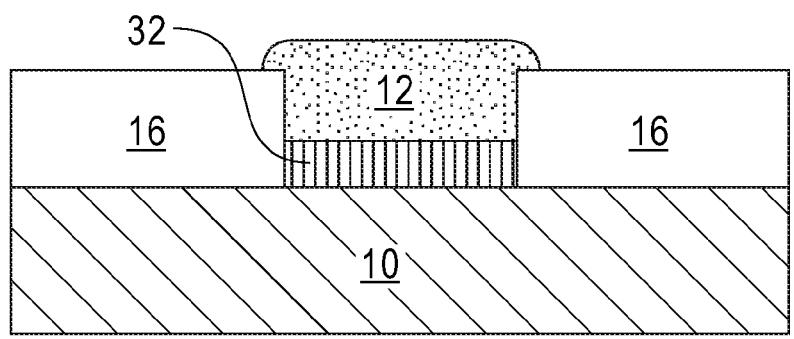
FIG. 2C is a cross-sectional view illustrating the epitaxial growth of a GaN material on the seed layer of the structure illustrated in FIG. 2B.

Referring to FIG. 2C, a GaN layer 12 is then epitaxially grown on the seed layer 32 to fill the gaps between all of the portions of the cladding layer 16. The GaN layer 12 is overgrown such that portions of the GaN layer 12 overlap with the top surfaces of the cladding layer 16.

Figure 2D:
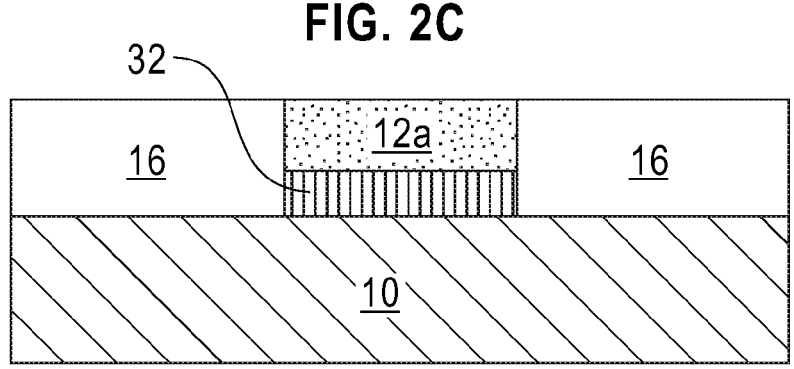
FIG. 2D is a cross-sectional view illustrating the planarization of the GaN material of the structure illustrated in FIG. 2C.

Referring now to FIG. 2D, the GaN layer 12 is then planarized using, for example, a CMP process such that the top surface of the GaN layer 12 is coplanar with the top surface of the cladding layer 16. A first portion of the planarized GaN layer 12 is now referred to as a first optical waveguide core portion 12a and a second portion of the planarized GaN layer 12 is now referred to as a second waveguide core portion 12b. The formation of the first optical waveguide 70 and the second optical waveguide 72 on the sapphire substrate 10 is now complete. The first waveguide core portion 12a of the first optical waveguide 70 and the second optical waveguide core portion 12b of the second optical waveguide 72 have an orthogonal configuration relative to each other in the present embodiment, but exemplary embodiments of the present application are not limited to this configuration.

After forming the first and second optical waveguides 70, 72, electronic devices (e.g., a light source and/or a photodetector) can now be co-integrated onto the same wafer as the first and second optical waveguides 70, 72 during the fabrication of the first semiconductor structure 1000. In some embodiments, the processes described in connection with FIGS. 1E-1I of the first embodiment may be performed in the present embodiment to form the light source 30 and a photodetector 40 on a sapphire substrate 10.

A microfluidic channel 20 may then be formed in the cladding layer 16 in the present embodiment in the same manner as discussed in connection with FIG. 1J. Next, the processes described in connection with FIG. 1K of the first embodiment to form the capping layer 50 on the support substrate 60 and the flip chip bonding of the capping layer 50 to the sapphire substrate 10, as well as the subsequent removal of the support substrate 60 after the flip chip bonding of the capping layer 50 to the sapphire substrate 10 may be performed in the present embodiment to provide the first semiconductor structure 1000 illustrated in FIGS. 1L-1N.

As discussed above in connection with the first embodiment, in the event it is not desired for the light source and/or photodetector to be formed during the fabrication of the first semiconductor structure 1000, but rather it is desired for them to be packaged externally, the steps in FIGS. 1E-1I may also be omitted in the present embodiment and the method could instead proceed from the processes described in connection with FIG. 2D to the processes described in connection with FIGS. 1J-1L to provide the first semiconductor structure 1000 illustrated in FIGS. 1L-1M.

A method of fabricating the second semiconductor structure 2000 according a third embodiment of the present application is described in connection with FIGS. 3A-3F, FIGS. 1E-1I and FIGS. 2A-2D.

Figure 3A:
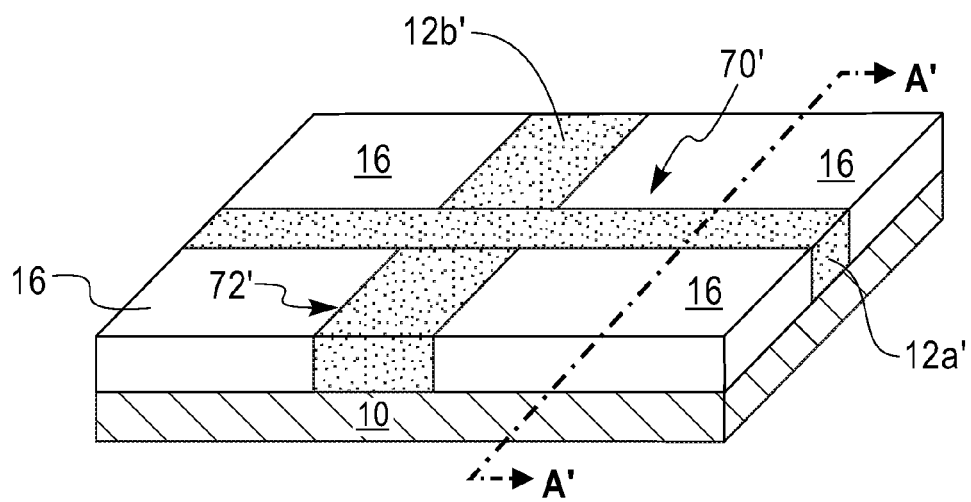
FIG. 3A is a perspective view illustrating a first optical waveguide and a second optical waveguide formed on a sapphire substrate in accordance with a third embodiment of the present application.
Figure 3B:
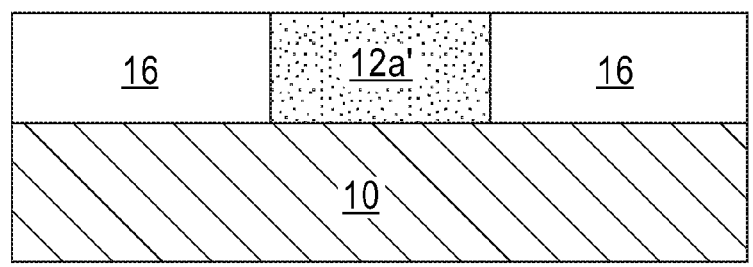
FIG. 3B is a cross-sectional view taken along line A'-A' through the cladding layer and the first optical waveguide core portion of the first optical waveguide.

The process for forming the second semiconductor structure 2000 begins with the forming of a first optical waveguide 70' and a second optical waveguide 72' on a sapphire substrate 10 as illustrated in FIGS. 3A-3B. The first optical waveguide 70' includes a first optical waveguide portion 12a' and the portions of a cladding layer 16 surrounding the first optical waveguide core portion 12a'. The second optical waveguide portion 72' includes a second optical waveguide core portion 12b' and the portions of the cladding layer 16 surrounding the second optical waveguide core portion 12b'.

The first optical waveguide 70' and the second optical waveguide 72' of the present embodiment illustrated in FIGS. 3A-3B may be formed by using either the same processes and materials as described in connection with FIGS. 1A-1D of the first embodiment or using substantially the processes and materials as described in connection with FIGS. 2A-2D of the second embodiment, except that in the present embodiment, the first optical waveguide core portion 12a' and the second optical waveguide core portion 12b' have a slightly different configuration than the first optical waveguide core portion 12a of the first optical waveguide 70 and the second optical waveguide core portion 12b of the second optical waveguide 72 of the first and second embodiments. Namely, the first optical waveguide core portion 12a' and the second optical waveguide core portion 12b' of the present embodiment are patterned in a manner such that the two optical waveguide portions intersect each other in a "cross-type" shape, whereas the first optical waveguide core portion 12a and the second optical waveguide core portion 12b of the first and second embodiments are patterned such that they are orthogonal relative to each other in a "L" shape configuration.

Figure 3C:
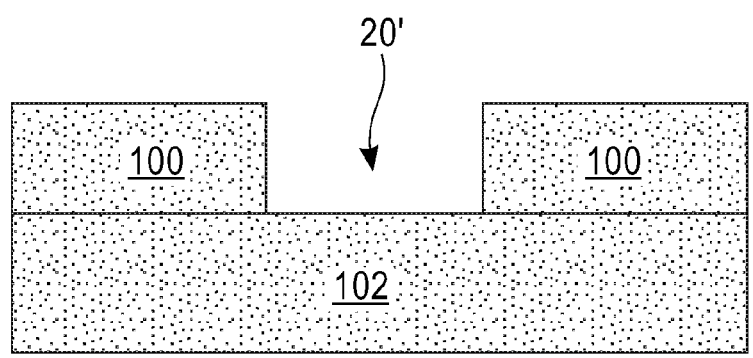
FIG. 3C is a cross-sectional view of the microfluidic channel formed in a patterned bonding layer located on a bonding substrate.

Now referring to FIG. 3C, a bonding layer (not shown) formed of, for example, Si or $SiO_2$, is epitaixally grown on a bonding substrate 102. In one embodiment, the bonding layer includes, $SiO_2$. An etching process such as, for example, an RIE or wet etching process is then performed on the bonding layer to form a patterned bonding layer 100 having a microfluidic channel 20' therein. The microchannel 20' of the present embodiment may have the same dimensions and structure as the microfluidic channel 20 discussed in connection with the first and second embodiments of the present application. Unlike the first and second embodiments, however, the microfluidic channel 20' of the present embodiment is formed on a separate substrate (e.g., bonding substrate 102) from the substrate (e.g., sapphire substrate 10) on which the first optical waveguide 70' and the second optical waveguide 72' are formed.

In particular, one of the wafers (e.g., either the bonding substrate 102 or the sapphire substrate 10) is inverted or flipped and bonded to the other using conventional flip chip bonding techniques known in the art. For example, in the present embodiment, the wafer including the bonding substrate 100 having the patterned bonding layer 100 and the microfluidic channel 20' formed thereon is flipped and bonded to wafer including the sapphire substrate 10 having the first optical waveguide 70' and the second optical waveguide 72' formed thereon to form the second semiconductor structure 2000 illustrated in FIGS. 3D-3E.

Figure 3D:
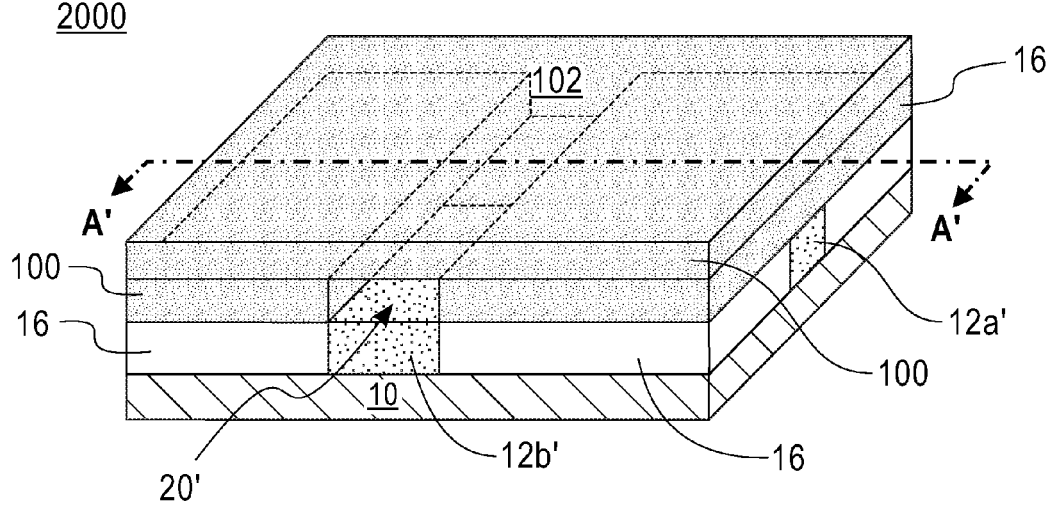
FIG. 3D is a perspective view of a second semiconductor structure.
Figure 3E:
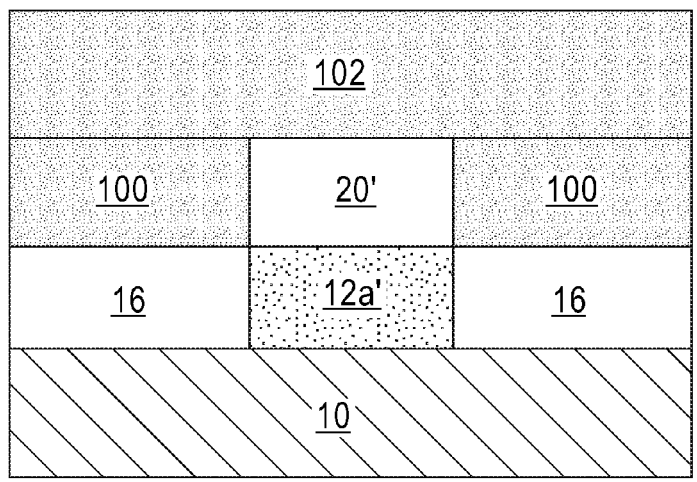
FIG. 3E is a cross-sectional view taken along line A'-A' through the bonding substrate, the bonding layer, the cladding layer, the first optical waveguide core portion and the sapphire substrate of the structure illustrated in FIG. 3B.

As shown in FIGS. 3D-3E, the patterned bonding layer 100 located on the bonding substrate 102 is bonded to the top surfaces of cladding layer 16 of the first and second optical waveguides 70', 72' such that the microfluidic channel 20' is located above the first optical waveguide 70' and the second optical waveguide 72' of the second semiconductor structure 2000.

Figure 3F:
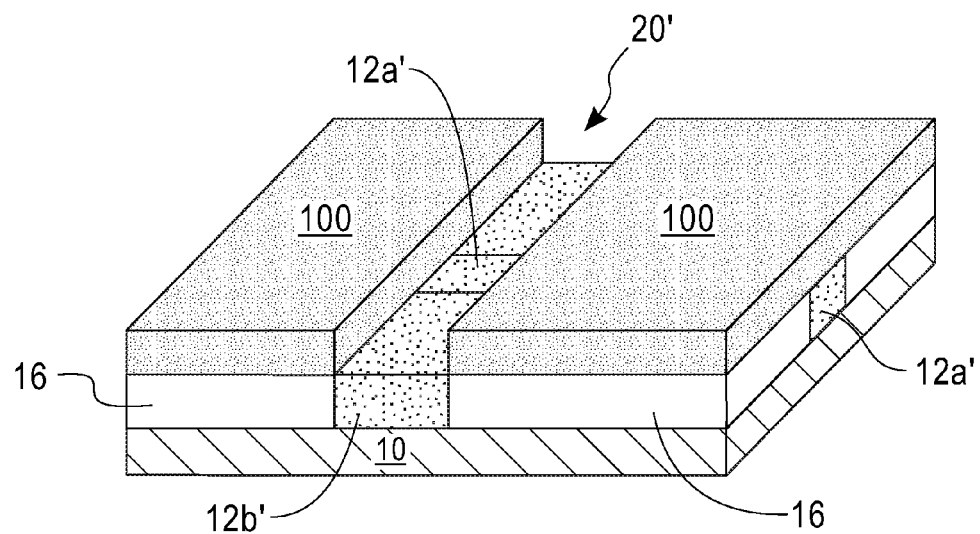
FIG. 3F is a perspective view of the second semiconductor structure with the bonding substrate removed.

Moreover, the final structure of the second semiconductor structure 2000 includes the bonding substrate 100 as illustrated in FIGS. 3D-3E but FIG. 3F illustrates the second semiconductor structure 2000 with the bonding substrate 102 removed for illustration purposes to show an even clearer view of the microfluidic channel 20'.

Alternatively, and in other embodiments, the patterned bonding layer 100 may be formed of silicon instead of $SiO_2$ in which case, a capping layer 50 similar to the capping layer 50 of the first and second embodiments would be formed on the top surface of the first optical waveguide 70' and the second optical waveguide 72' in similar fashion as illustrated in FIG. 1K prior to flip chip bonding the structure including the patterned bonding layer 100 and the microfluidic channel 20' located on the bonding substrate 102 onto the sapphire substrate 10 including the first and second optical waveguides 70', 72'. In this case, one of the wafers would be flipped and the patterned bonding layer 100 located on the bonding substrate 102 would be bonded to the capping layer 50 located on the first and second optical waveguides 70', 72' of the sapphire substrate 10 to form the second semiconductor structure 2000.

The operation of the second semiconductor structure 2000 may be performed in substantially the same manner as the first semiconductor structure 1000 of the first and second embodiments, except that in the present embodiment, the microfluidic channel 20' of the second semiconductor structure 2000 is formed above the first optical waveguide 70' and the second optical waveguide 72'.

For example, in the present embodiment, excitation light (e.g., UV light) is emitted from a light source and the excitation light is scattered up by the first optical waveguide core portion 12a' of the first optical waveguide 70' operatively connected to the light source and into the microfluidic channel 20' where it is absorbed by fluorescent particles (e.g., particles which emit fluorescent light in the UV range) attached to an analyte (e.g., DNA, RNA, viruses, or proteins). Further, the excitation light absorbed by the particles are then scattered in different directions including to the second optical waveguide portion 12b' of the second optical waveguide 72' which in turn guides the light to a photodetector operatively connected to the second optical waveguide 72'. In addition, some of the excitation light in the microfluidic channel 20' not absorbed by fluorescent particles attached to the analyte may also be scattered into the second waveguide core portion 12b' and the cladding layer 16 of the second optical waveguide 72' by, for example, inert particles or air bubbles in the microfluidic channel 20'.

A light source and/or a photodetector may be co-integrated with the first and second optical waveguides 70', 72' and microfluidic channel 20' during the fabrication of the second semiconductor structure 2000 in similar fashion as discussed above in connection with the forming of the light source 30 and the photodetector 40 of the first semiconductor structure 1000 of the first and second embodiments. Alternatively, electronic devices such as a light source and/or a photodetector may be formed in a separate process from the fabrication of the second semiconductor structure 2000 in the manner described in connection with the first and second embodiments.

Referring now to FIGS. 4A-4E, a method for fabricating a third semiconductor structure 3000 according to a fourth exemplary embodiment of the present application is described. The third semiconductor 3000 is substantially similar to the second semiconductor structure 2000 of the third exemplary embodiment except that the first optical waveguide 70a and the second optical waveguide 72a of the present embodiment have a different configuration than that of the first optical waveguide 70' and the second optical waveguide 72' of the second semiconductor structure 2000, and in addition the third semiconductor structure 3000 further includes a cladding reflector portion 16a.

Figure 4A:
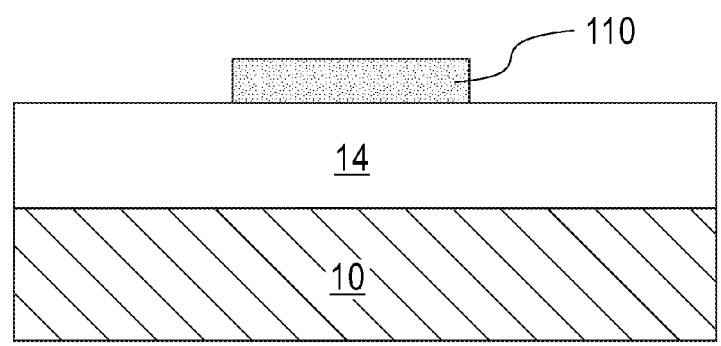
FIG. 4A is a cross-sectional view of a photoresist on a cladding material located on a sapphire substrate according to a fourth exemplary embodiment.

Referring now to FIG. 4A, a cladding material 14 including, for example, $SiO_2$ may be deposited on a sapphire substrate 10 in the same manner as described in connection with the second semiconductor structure 2000 of the third embodiment. A photoresist 110 is then formed on the cladding material 14 using conventional techniques known in the art.

Figure 4B:
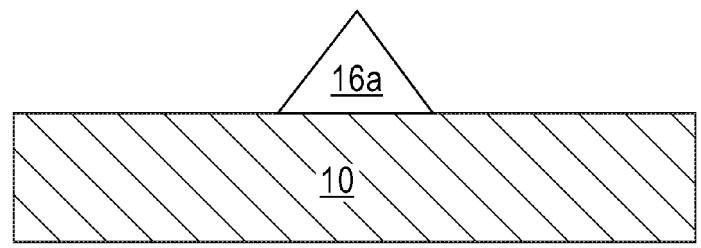
FIG. 4B is a cross-sectional view of the etching of the cladding material of the structure illustrated in FIG. 4A.

Referring now to FIG. 4B, a portion of the cladding material 14 is then etched utilizing an isotropic wet etching or isotropic plasma etching process using the photoresist 110 as an etching mask to form a cladding reflector portion 16a having a tapered shape on the sapphire substrate 10. In the present embodiment, the cladding reflector portion 16a has a pyramid type shape but exemplary embodiments of the present application are not limited thereto. The remainder of the cladding material 14 not having the tapered shape of the cladding reflector portion 16a is transformed into cladding layer 16 as a result of the isotropic etching.

Figure 4C:
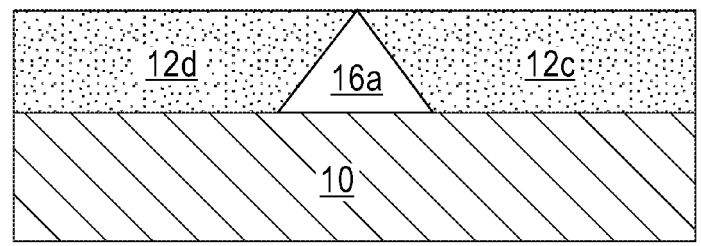
FIG. 4C is a cross-sectional view of the forming of a first optical waveguide and a second optical waveguide on the structure illustrated in FIG. 4I.

Referring now to FIG. 4C, a seed layer (not shown) formed of, for example, aluminum nitride (AlN), can then be disposed on areas of the sapphire substrate 10 not occupied by the cladding reflector portion 16a and the cladding layer 16. A GaN material (not shown) is then epitaxially grown on the seed layer to fill all areas on top surface of the sapphire substrate 10 not occupied by the cladding reflector portion 16a and the cladding layer 16. The GaN material is then planarized in substantially the same manner as described above in connection with FIG. 2D of the second embodiment such that the top surface of the GaN material is coplanar with the top surface of the first cladding layer 16 and a top surface of the cladding reflector portion 16a to complete the formation of the first optical waveguide 70a and the second optical waveguide 72a. A first portion of the planarized GaN material is now referred to as a first optical waveguide core portion 12c and a second portion of the planarized GaN material is now referred to as a second optical waveguide core portion 12d.

The first optical waveguide 70a includes the first optical waveguide core portion 12c and the portions of the cladding layer 16 laterally surrounding the first optical waveguide core portion 12c. The second optical waveguide 72a includes the second optical waveguide core portion 12d and the portions of the cladding layer 16 laterally surrounding the second optical waveguide core portion 12d. The first optical waveguide core portion 12c and the second optical waveguide core portion 12d are located on side surfaces of the cladding reflector portion 16a such that the cladding reflector portion 16a is located in between the first optical waveguide core portion 12c and the second optical waveguide core portion 12d.

The first waveguide core portion 12c and the second optical waveguide core portion 12d have a configuration in which they are entirely on a same plane each other in the present embodiment but exemplary embodiments of the present application are not limited to this configuration.

Further, a patterned bonding layer 100 having a microfluidic channel 20' formed therein is formed on a bonding substrate 102 in the same manner as discussed in connection with FIG. 3C of the third embodiment. The wafer including the bonding substrate 102 having the patterned bonding layer 100 and the microfluidic channel 20' formed thereon may then be flipped and bonded to wafer including the sapphire substrate 10 having the first optical waveguide 70a and the second optical waveguide 72a formed thereon to form the third semiconductor structure 3000 illustrated in FIG. 4D-4E.

Figure 4D:
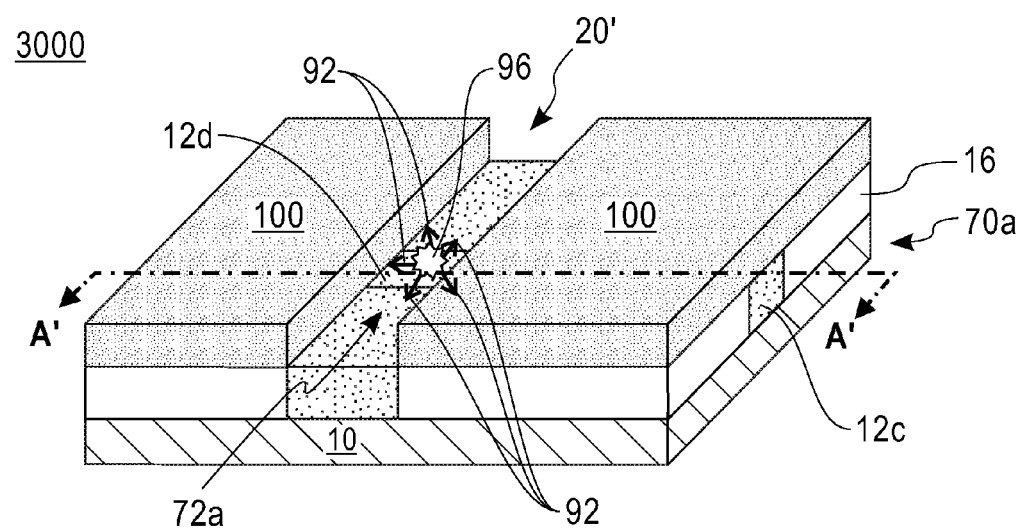
FIG. 4D is a perspective view of a third semiconductor structure according to the fourth exemplary embodiment of the present application.
Figure 4E:
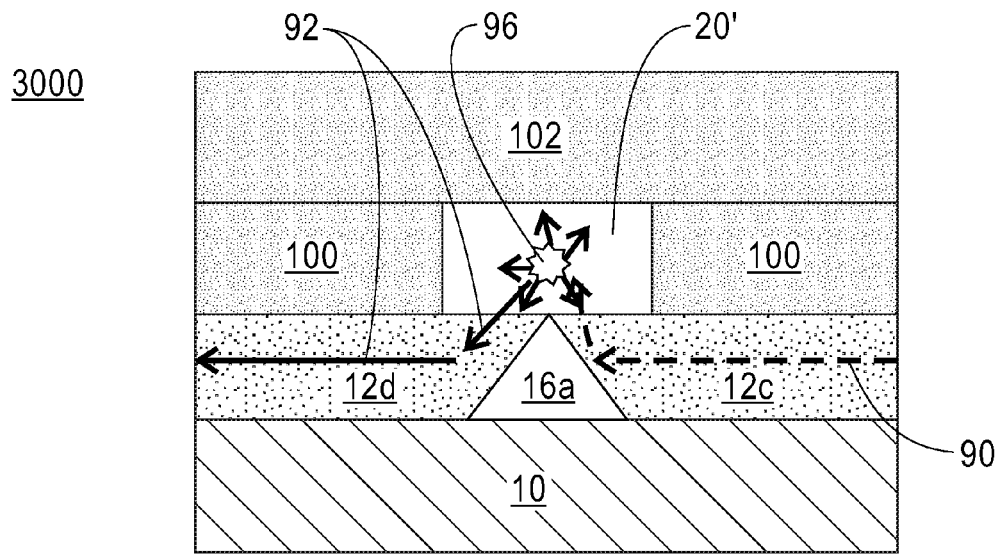
FIG. 4E is a cross-sectional view taken along line A'-A' through the bonding substrate, the patterned bonding layer, the microfluidic channel, the first optical waveguide and the second optical waveguide, and the cladding reflector portion of the structure illustrated in FIG. 4D.

It is noted that the final structure of the third semiconductor structure 3000 includes the bonding substrate 102 as illustrated in FIG. 4E, but FIG. 4D, for illustrative purposes shows the third semiconductor structure 3000 with the bonding substrate 102 removed to show an even clearer view of the microfluidic channel 20'.

The operation of the third semiconductor structure 3000 is very similar to the first semiconductor structure 1000 and the second semiconductor structure 2000, except for a variation in how excitation light is guided into the microfluidic channel.

For example, in the third semiconductor structure 3000 of the present embodiment, an excitation light 90 (e.g., a UV light) emitted from a light source is guided through the first waveguide core portion 12c of the first optical waveguide 70a and then this excitation light 90 exits the first optical waveguide core portion 12c of the first optical waveguide 70a to then be reflected by the cladding reflector portion 16a up into microfluidic channel 20' based upon the phenomenon of total internal reflection. Some of the excitation light 90 reflected into the microfluidic channel 20' is absorbed by particles 96 (e.g., particles which emit fluorescent light in the UV range) attached to an analyte (e.g., DNA, RNA, viruses, or proteins) flowing in the microfluidic channel 20'. Further, the excitation light 90 absorbed by the particles 96 in the microfluidic channel 20' are then scattered as fluorescent UV light 92 in different directions including into the second optical waveguide core portion 12d of the second optical waveguide 72a. The second optical waveguide core portion 12d, in turn, guides the fluorescent UV light 92 into a photodetector operatively connected to the second optical waveguide 72a. In addition, some of the excitation light 90 in the microfluidic channel 20' not absorbed by particles 96 attached to the analyte may also be scattered into the second waveguide core portion 12d and the cladding layer 16 of the second optical waveguide 72a or into other areas of the microfluidic channel 20' by, for example, inert particles, air bubbles or other types of irregularities in the microfluidic channel 20'.

Figure 5:
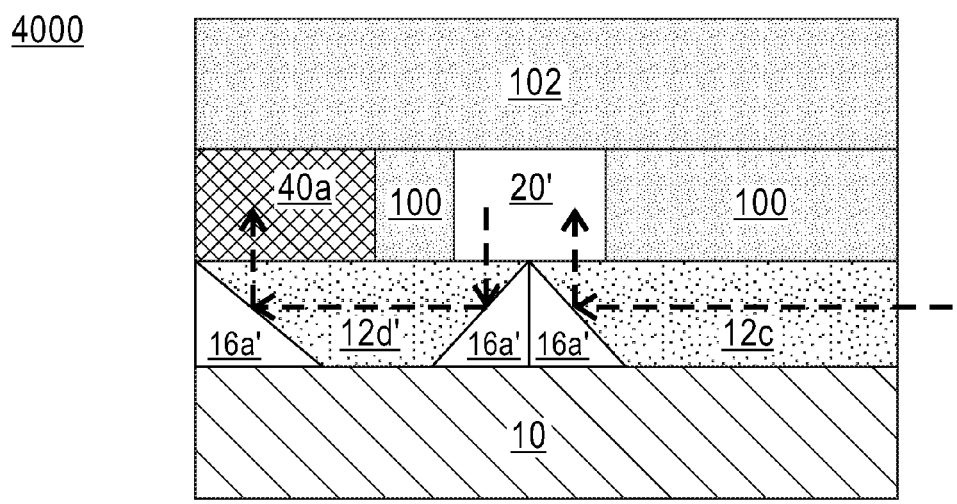
FIG. 5 is a cross-sectional view of a fourth semiconductor structure according to a fifth exemplary embodiment of the present application.

Now referring to FIG. 5, there is illustrated a fourth semiconductor structure 4000 according to a fifth embodiment of the present application. The fourth semiconductor structure 4000 has a similar structure to the third semiconductor structure 3000 except that the fourth semiconductor structure 4000 includes a plurality of cladding reflector portions 16a' having a slightly different configuration than the cladding reflector portion 16a of the third semiconductor structure 3000. However, the fourth semiconductor structure 4000 and the third semiconductor structure 3000 may be formed using many of the same processes as one another including similar photolithography and etching techniques as discussed above in connection with the forming of the cladding reflector portion 16a of the third semiconductor structure 3000. The first optical waveguide core portion 12c and the second optical waveguide core portion 12d of the third semiconductor structure 3000 are essentially the same as the first optical waveguide core portion 12c and the second optical waveguide core portion 12d', except that the shape of the second optical waveguide core portion 12d' of the fourth semiconductor structure 4000 is slightly different than the shape of the second optical waveguide core portion 12d of the third semiconductor structure 3000 due to the pattern of the cladding reflector portions 16a' of the fourth semiconductor structure 4000.

In addition, in forming the fourth semiconductor structure 4000 illustrated in FIG. 5, a photodetector 40a and microfluidic channel 20' are formed in a patterned bonding layer 100 located on a bonding substrate 102, and then the wafer including the patterned bonding layer 100, the microfluidic channel 20' and the photodetector 40a located on the bonding substrate 102 may be flipped and bonded to the wafer including the first optical waveguide core portion 12c and the second optical waveguide core portion 12d' located on the sapphire substrate 10. Alternatively, and in other embodiments, the wafer including the first optical waveguide core portion 12c and the second optical waveguide core portion 12d' located on the sapphire substrate 10 may instead be flipped and bonded to wafer including the patterned bonding layer 100, the microfluidic channel 20' and the photodetector 40a located on the bonding substrate 102.

In the present embodiment, the patterned bonding layer 100 and the bonding substrate 102 are formed of, for example, silicon. Moreover, the photodetector 40a formed in the patterned bonding layer 100 formed of silicon may be formed using conventional techniques known in the art.

The operation of the fourth semiconductor 4000 is very similar to the operation of the third semiconductor structure 3000 except that light (e.g., fluorescent UV light or excitation light) exiting the second optical waveguide core 12d' of the fourth semiconductor structure 4000 is reflected by one of the cladding reflector portions 16a' and upward into the photodetector 40a.

With exemplary embodiments of the present application, the providing of optical waveguides having a core portion formed of GaN which has minimal absorption in the UV/visual range allows these optical waveguides to be used for these wavelengths.

In addition, with exemplary embodiments, microfluidic channels integrated with optical waveguides and electronic devices (e.g., light sources and photodetectors) on the same wafer allow for simplified optical analysis methods. Moreover, with exemplary embodiments of the present application, waveguides, combined with microelectronic light sources (e.g., laser, light emitting diodes) and photodetectors (e.g., PIN diode, and avalanche photodiode diode), allow for miniaturized detection or analysis schemes integrated on a single chip (as opposed to conventional lab or bench top scale setups).

While the present application has been described in terms of specific embodiments, it is evident in view of the foregoing description that numerous alternatives, modifications and variations will be apparent to those skilled in the art. Each of the various embodiments of the present application can be implemented alone, or in combination with any other embodiments of the present application unless expressly disclosed otherwise or otherwise impossible as would be known to one of ordinary skill in the art. Accordingly, the present application is intended to encompass all such alternatives, modifications and variations which fall within the scope and spirit of the present application and the following claims.

What is claimed is:

1. A method of forming a semiconductor structure, said method comprising:
    forming a first optical waveguide and a second optical waveguide on a sapphire substrate, wherein the first optical waveguide and the second optical waveguide each include a core portion of gallium nitride (GaN), and a cladding layer laterally surrounding the core portion, wherein the cladding layer includes a material having a refractive index less than a refractive index of the sapphire substrate;
    etching a portion of the cladding layer to form a microfluidic channel in the cladding layer; and
    forming a capping layer on a top surface of the first optical waveguide, the second optical waveguide and the microfluidic channel, wherein the cladding layer and the capping layer each include one of silicon oxide (SiO$_2$) or glass, and wherein the first optical waveguide and the second optical waveguide are formed on the sapphire substrate by:
        epitaxially growing a GaN layer on a seed layer located on the sapphire substrate;
        etching the GaN layer to form the first optical waveguide core portion and a second optical waveguide core portion on the sapphire substrate;
        depositing a cladding material on the sapphire substrate to backfill substantially all areas on the top surface of the sapphire substrate not occupied by the first optical waveguide core portion, the second optical waveguide core portion, and the seed layer with the cladding material; and
        planarizing the cladding material to form the cladding layer, wherein a top surface of the cladding layer is coplanar with a top surface of the first optical waveguide core and a top surface of the second optical waveguide core.

2. The method of claim 1, wherein the seed layer includes aluminum nitride.

3. The method of claim 1, wherein the GaN is deposited using one of metal organic chemical vapor deposition (MOCVD) or molecular beam epitaxy (MBE).

4. The method of claim 1, wherein prior to forming the microfluidic channel, the method further comprises:
    forming at least one of a light source and a photodetector on the sapphire substrate.

5. The method of claim 4, wherein the light source is formed by:
    etching a region of the cladding layer to expose a portion of the top surface of the sapphire substrate;
    depositing a seed layer on the exposed portion of the top surface of the sapphire substrate;
    forming a lower GaN layer having a first conductivity type on the seed layer;
    forming an upper GaN layer having a second conductivity type, which differs from the first conductivity type, on the lower GaN layer;
    etching a portion of the upper GaN layer to expose a portion of a top surface of the lower GaN layer; and
    forming, in any order, a first contact on the upper GaN layer, and a second contact on the lower GaN layer.

6. The method of claim 1, wherein the capping layer is deposited on the top surface of the first waveguide, the second waveguide and the microfluidic channel by:
    forming the capping layer on a top surface of a support substrate;
    flipping one of the support substrate or the sapphire substrate and bonding the capping layer of the support substrate to the top surfaces of the first waveguide, the second waveguide and the microfluidic channel of the sapphire substrate in a flip chip bonding process; and
    removing the support substrate from the capping layer after the flip chip bonding process.

* * * * *